(12) United States Patent
Kappes et al.

(10) Patent No.: US 7,622,300 B2
(45) Date of Patent: Nov. 24, 2009

(54) TRANS-LENTIVIRAL VECTOR PARTICLES AND TRANSDUCTION OF EUKARYOTIC CELLS THEREWITH

(76) Inventors: John C. Kappes, 5284 Birdsong Rd., Birmingham, AL (US) 35242; Xiaoyun Wu, 4217 Heritage Oaks Cir., Birmingham, AL (US) 35242

( * ) Notice: Subject to any disclaimer, the term of this patent is extended or adjusted under 35 U.S.C. 154(b) by 740 days.

(21) Appl. No.: 10/202,457

(22) Filed: Jul. 24, 2002

(65) Prior Publication Data

US 2003/0072938 A1   Apr. 17, 2003

Related U.S. Application Data

(63) Continuation of application No. 09/709,751, filed on Nov. 10, 2000, now abandoned, which is a continuation-in-part of application No. 09/460,548, filed on Dec. 14, 1999, now Pat. No. 6,555,342, which is a continuation-in-part of application No. 09/089,900, filed on Jun. 3, 1998, now abandoned.

(60) Provisional application No. 60/164,626, filed on Nov. 10, 1999.

(51) Int. Cl.
*C12N 15/867* (2006.01)
*C12N 15/56* (2006.01)

(52) U.S. Cl. .................. 435/455; 435/69.1; 435/320.1; 435/456; 536/23.1; 536/23.4; 536/23.72; 536/24.1

(58) Field of Classification Search .............. 435/320.1, 435/69.1, 455, 456, 457, 325, 366; 424/93.1, 424/93.2, 93.6; 536/23.1, 23.72, 24.1
See application file for complete search history.

(56) References Cited

U.S. PATENT DOCUMENTS

| | | | |
|---|---|---|---|
| 5,175,099 A | 12/1992 | Willis | |
| 5,378,806 A | 1/1995 | Willis | |
| 5,665,577 A | 9/1997 | Sodroski et al. | |
| 5,861,161 A | 1/1999 | Cohen et al. | |
| 5,981,276 A | 11/1999 | Sodroski et al. | |
| 6,043,081 A | 3/2000 | Cohen et al. | |
| 6,365,150 B1 | 4/2002 | Leboulch et al. | |
| 6,602,705 B1 | 8/2003 | Barnett et al. | |

FOREIGN PATENT DOCUMENTS

| | | |
|---|---|---|
| DE | 275259 | 1/1990 |
| EP | 356021 | 2/1990 |
| WO | WO 90/15875 | 12/1990 |
| WO | WO 92/00987 | 1/1992 |
| WO | WO 93/24632 | 12/1993 |
| WO | WO 93/25235 | 12/1993 |
| WO | WO 94/17825 | 8/1994 |
| WO | WO 95/16705 | 6/1995 |
| WO | WO 95/26361 | 10/1995 |
| WO | WO 96/07741 | 3/1996 |
| WO | WO 96/11696 | 4/1996 |
| WO | WO 96/32494 | 10/1996 |
| WO | WO 97/36481 | 10/1997 |
| WO | WO 99/51754 | 10/1999 |
| WO | WO 99/58701 A1 | 11/1999 |
| WO | WO 00/39302 | 7/2000 |

OTHER PUBLICATIONS

Banerjee et al., Biochimica et Biophysica Acta, 2000, vol. 1480, pp. 1-5.*
Groth et al., J. Mol. Biol., 2004, vol. 335, pp. 667-678.*
Daboussi, Genetica, 1997, vol. 100, pp. 253-260.*
Bennett, Journal of Antimicrobial Chemotherapy, 1999, vol. 43, pp. 1-4.*
Kempkin et al., BioEssays, 1998, vol. 20, pp. 652-659.*
Zhu et al., J. Virol., 2004, vol. 78, No. 10, pp. 5045-5055.*
Akari, et al., "Biological Characterization Of Human Immunodeficiency Virus Type 1 and 2 Mutants In Human Perizheral Blood Mononuclear Cells," *Arch. Virol.*, 1992, pp. 157-167, vol. 123.
Akkina, et al. "High-Efficiency Gene Transfer into CD34+ Cells with a Human Immunodeficiency Virus Type 1-Based Retroviral Vector Pseudotyped with Vesicular Stomatitis Virus Envelope Glycoprotein G," *J. Virol.*, 1996, pp. 2581-2585, vol. 70.
Alton, et al., "Nucleotide Sequence Analysis of the Chloramphenicol Resistance Transposon Tn9," *Nature*, 1979, pp. 282:864-869, vol. 282.
Amado, et al., "Lentiviral Vectors—the Promise of Gene Therapy within Reach?," *Science*, 1999, pp. 674-676, vol. 285.
Ansari-Lari, et al., "Expression of Human Immunodeficiency Virus Type I Reverse Transcriptase in Trans During Virion Release and after Infection," *J. Virol.*, 1996, pp. 3870-3875, vol. 70.

(Continued)

*Primary Examiner*—Eileen B O Hara
(74) *Attorney, Agent, or Firm*—Bradley Arant Boult Cummings LLP

(57) ABSTRACT

Trans-lentiviral gene transfer vectors, vector systems, vector particles, and methods for transduction of primary nondividing cells using the same, are described. Further described are modifications to the gene transfer vectors that improve transduction efficiency and/or gene expression, e.g., by incorporating the cis-acting sequences, PPT-CTS and/or WPRE, and derivatives or analogs thereof.

43 Claims, 7 Drawing Sheets

OTHER PUBLICATIONS

Ansari-Lari, et al., "Analysis of Human Immunodeficiency Virus Type I Integrase Mutants," *Virology*, 1995, pp. 332-335, vol. 70.

Balotta, et al., "Antisense Phosphorothioate Oligodeoxynucleotides Targeted to the vpr Gene Inhibit Human Immunodeficiency Virus Type I Replication in Primary Human Macrophages," *J. Virol.*, 1993, pp. 4409-4404, vol. 67.

Bukovsky, et al., "Lack of Integrase Can Markedly Affect I Human Immunodeficiency Virus Typed Particle Production in Presence of an Active Viral Protease," *J. Virol.*, 1996, pp. 6820-6725, vol. 70.

Charneau, et al., "A Second Origin of DNA Plus-Strand Synthesis Is Required for Optimal Human Immunodeficiency Virus Replication," 1992, pp. 2814-2820, vol. 66.

Charneau, et al., "HIV-1 Reverse Transcription: A Termination Step at the Center of the Genome," *J. Mol. Biol.*, 1994, pp. 651-662, vol. 241.

Cohen, et al., "Human Immunodeficiency Virus vpr Product Is a Virion-Associated Regulatory Protein," *J. Virol.*, 1990, pp. 3097-3099, vol. 64.

Cohen, et al., "Identification of HIV-1 vpr Product and Function," *J. Acq. Immune Def. Synd.*, 1990, pp. 11-18, vol. 13.

Dedera, et al., "Viral Protein R of Human Immunodeficiency Virus Types 1 and 2 Is Dispensable for Replication and Cytopathogenicity in Lymphoid Cells," *J. Virol.*, 1989, pp. 3205-3208, vol. 63.

Derosiers, "HIV with Multiple Gene Deletions as a Live Attenuated Vaccine for AIDS," *AIDS Research and Human Retroviruses*, 1992, pp. 441-421, vol. 8.

Di Marzio, et al., "Mutational Analysis of Cell Cycle Arrest, Nuclear Localization, and Virion Packaging of Human Immunodeficiency Virus Type 1 Vpr," *J. Virol.*, 1995, pp. 7909-7916, vol. 69.

Dull, et al., "A Third-Generation Lentivirus Vector with a Conditional Packaging System," *J. Virol.*, 1998, pp. 8463-8471, vol. 72.

Engelman, et al., "Multiple Effects of Mutations in Human Immunodeficiency Virus Type 1 Interase on Viral Replication," *J. Virol.*, 1995, pp. 2729-2736, vol. 69.

Finer, et al., "kat: A High-Efficiency Retroviral Transduction System for Primary Human T Lymphocytes," *Blood*, 1994, pp. 43-50, vol. 83.

Fletcher, T.M, III, et al., "Complementation of Integrase Function in HIV-1 Virons," *The EMBO Journal*, 1997, pp. 5123-5138, vol. 16(16).

Fletcher, T.M. III, et al., "Complementation of Integrase Function in HIV-1 Virons," Fourth Conference on Retroviruses and Opportunistic Infections, Jan. 22, 1997, Abstract No. 394.

Fletcher, T.M. III, et al., "Complementation of Integrase Functon in HIV-1 Virons," Third Conference on Retroviruses and Opportunistic Infections, Jan. 28, 1996.

George, et al., "Current Methods in Sequence Comparison and Analysis," *Macromolecule Sequencing and Synthesis, Selected Methods and Applications* pp. 127-149.

Gibbs, et al., Construction and In Vitro Properties of SIV MAC Mutants with Deletions in "Nonessential" *Genes AIDS Research and Human Retroviruses*, 1994, pp. 607-616 vol. 10.

Gottlinger, et al., "Effect of Mutations Affecting the p6 Gag Protein on Human Immunodeficiency Virus Particle Release," *Proc. Natl. Acad. Sci.*, 1991, pp. 3195-3199, vol. 88.

Guyader, et al., "VPX Mutants Of HIV-2 Are Infectious in Established Cell Lines But Display A Severe Defect In Peripheral Blood Lymphocytes," *EMBO Journal*, 1989, pp. 1169-1175, vol. 8(4).

Hattori, et al., "The HIV-2 Vpr Gene is Essential for Macrophage Infections," p. 309 (Abstract).

Hattori, et al., "The Human Immunodeficiency Virus Type 2 vpr Gene is Essential for Productive Infection of Human Macrophages," *Proc. Natl. Acad. Sci. USA*, 1990, pp. 8080-8084, vol. 87.

He, et al., "Human Immunodeficiency Virus Type 1 Viral Protein R (Vpr) Arrests Cells in the G2 Phase of the Cell Cycle by Inhibiting p34cdc2 Activity," *J. Virol.*, 1995, pp. 6705-6711, vol. 69(11).

Heinzinger, et al., "The Vpr Protein Of Human Immunodeficiency Virus Type 1 Influences Nuclear Localization Of Viral Nucleic Acids In Nondividing Host Cells," *Proc. Natl. Acad. Sci. USA*, 1994, pp. 7311-7315, vol. 91.

Hoch, et al., "The Vpr Deletion Mutant of Simian Immunodeficiency Virus Induces AIDS in Rhesus Monkeys," *J Virol.* 1995, pp. 4807-4813, vol. 69(8).

Horton, et al., "HIV-2 Viral Protein X Association with Gagp27 Capsid Protein," *Virology*, 1994, pp. 453-457, vol. 199.

Hu, et al., Mutational Analysis of the Murine IDS-Defective Viral Genome Reveals a High Reversion Rate in Vivo and a Requirement for an Intact Pr60faf Protein for Efficient Induction of Disease, *Journal of Virology*, 1995, pp. 60-68.

Huang, et al., "Mutational Analysis of the Murine AIDS-Defective Viral Genome Reveals a High Reversion Rate In Vivo and a Requirement for an Intact Pr60gag Protein for Efficient Induction of Disease," *J. Virol.*, 1995, pp. 60-68.

Huang, et al., "P6Gag Is Required for Particle Production from Full-Length Human Immunodeficiency Virus Type 1 Molecular Clones Expressing Protease," *J. Virol.*, 1995, pp. 6810-6818.

Hutchinson, et al., "Utagenesis at a Specific Position in a DNA Sequence," *J. Biol. Chem.* p. 6551, vol. 253.

Kafri, et al., "Sustained Expression of Genes Delivered Directly into Liver and Muscle by Lentiviral Vectors," *Nature Genetics*, 1997, pp. 314-317, vol. 17.

Kappes, et al., Human Immunodeficiency Virus Type 2 vps Protein Augments Viral Infectivity, *J. Virol.*, 1991, pp. 197-209, vol. 184.

Kappes, et al., "Identification of a Novel Retroviral Gene Unique to Human Immunodeficiency Virus Type 2 and Simian Immunodeficiency Virus SIV MAC," *J. Virol.*, pp. 3501-3504, vol. 193.

Kappes, et al., "Intracellular Transport and Virion Incorporation of vpx Requires Interaction with other Virus Type-Specific Components," *J. Virol.*, 1993, pp. 222-223, vol. 193.

Kappes, et al., "Targeting Foreign Proteins to HIV Particles Via Fusion with Vpr and Vps," *J. Biol. Chem. Suppl.*, 1994, p. 395, vol. 21(A).

Kappes, et al., "The HIV Vpx and Vpr Genes Mediate Virion Incorporation of Nuclease Fusion Proteins," *J. Biol. Chem. Suppl.*, 1995, p. 162, vol. 21(A).

Kappes, J.C., et al., "Infectious Human Immunodeficiency Virus Type 1 Derived From Reverse Transcriptase (RT) and Integrase (IN) Minus Provirus *Trans* Complemented with VPR—Rt and -IN Fusion Protein," Keystone Symposia, Apr. 8, 1997.

Kewalramani, et al., "Protein Stability Influences Human Immunodeficiency Virus Type 2 Vpr Virion Incorporation and Cell Cycle Effect," *Virology*, 1996, pp. 326-334, vol. 218.

Kewalramani, et al., "Vpx Association with Mature Core Structures of HIV-2," *Virology*, 1996, pp. 159-168, vol. 218.

Kirchoff, et al., "Upstream U3 Sequences in Simian Immunodeficiency Virus are Selectively Deleted in Vivo in the Absence of an Intact nef Gene," *J. Virol.*, 1994, pp. 2031-2037, vol. 68, No. 3.

Kondo, et al., "The p6gag Domain of Human Immunodeficiency Virus Type 1 is Sufficient for the Incorporation of Vpr into Heterologous Viral Particles," *J. Virol.*, 1995, pp. 2759-2764, vol. 69, No. 5.

Lang, et al., "Importance of vpr for Infection of Rhesus Monkeys with Simian Immunodeficiency Virus," *J. Virol.*, 1993, pp. 902-912, vol. 67, No. 2.

Lavallee, et al., "Requirement of the Pr55gag Precursor for Incorporation of the VPR Production into Human Immunodeficiency Virus Type 1 Viral Particles," *J. Virol.*, 1994, pp. 1926-1934, vol. 68, No. 3.

Lee, et al., "The Role of vpx in the Life Cycle of HIV-2," submitted to the *Proceedings of the Third Annual "Colloque Des Cent Gardes,"* 1998.

Levy, et al., "Extracellular Vpr Protein Increases Cellular Permissiveness to Human Immunodeficiency Virus Replication and Reactivates Virus from Latency," *J. Virol.*, 1995, pp. 1243-1252, vol. 69, No. 2.

Levy, et al., "Induction of Cell Differentiation by Human Immunodeficiency Virus 1 vpr," *Cell*, 1993, pp. 541-550, vol. 72.

Levy, et al., "Serum Vpr Regulates Productive Infection And Latency Of Human Immunodeficiency Virus Type 1," *Proc. Natl. Acad. Sci. USA*, 1994, pp. 10873-10877, vol. 91.

Liu, et al., "Incorporation of Functional Human Immunodeficiency Virus Type 1 Integrase into Virions Independent of the Gag/Pol Precursor Protein," *J. Virology*, 1997, pp. 7704-7710, vol. 71 (Revised Manuscript, #JVI 548-97).

Liu, et al., "The Vif Protein of Human and Simian Immunodeficiency Viruses is Packaged into Virions and Associates with Viral Core Structures," *J. Virol.*, pp. 7630-7638, vol. 69.

Liu, H., et al., Replication of Integrase Mutant HIV-1 Complemented in Trans With Heterologous in Protein, Cold Spring Harbor Meeting on Retroviruses, May 20, 1997.

Lu, et al.., "A Leucine Triplet Repeat Sequence (LXX)4 in p6gag is Important for Vpr Incorporation into Human Immunodeficiency Virus Type 1 Particles," *J. Virol.*,1995, pp. 6873-6879, vol. 69.

Lu, et al., "Human Immunodeficiency Virus Type 1 Viral Protein R Localization in Infected Cells and Virions," *J. Virol.*, 1993, pp. 6542-6552, vol. 67(11).

MacReadie, et al., "A Domain of Human Immunodeficiency Virus Type 1 VPR containing repeated H(S/F)RIG Amino Acid Motifs Causes Cell Growth Arrest and Structural Defects," *Proc. Natl. Acad. Sci USA*, 1995, pp. 2770-2774, vol. 92.

Mahalingam, et al., "Functional Analysis of HIV-1 Vpr: Identification of Determinants Essential for Subcellular Localization," *Virol.*, 1995, pp. 331-339, vol. 212.

Mahalingam, et al., HIV-1 VPR Interacts with Human 34-kDa mov34 Homologue, a Cellular Factor Linked to the G2/M Phase Transition of the Mammalian Cell Cycle, *Proc. Natl. Acad. Sci. USA*, 1998, pp. 3419-3424, vol. 95.

Mahalingam, et al., Identification of Residues in the N-Terminal Acidic Domain of HIV-1 Vpr Essential for Virion Incorporation, *Virology*, 1995, pp. 647-652, vol. 214.

Mahalingam, et al., "The Carboxy-Terminal Domain is Essential for Stability and not for Virion Incorporation of HIV-1 Vpr into Virus Particles," *Virol.*, 1995, pp. 647-652, vol. 214.

Marcon, et al., "Dispensible Role of the Human Immunodeficiency Virus Type 2Vpx Protein in Viral Replication," *J. Virol.*, 1991, pp. 3938-3942, vol. 65(7).

Matsuda, et al., A Viron-Specific Inhibitory Molecule With Therapeutic Potential For Human Immunodeficiency Virus Type 1, *Proc. Natl. Acad .Sci USA*, 1993, pp. 3544-3548, vol. 90.

Miyoshi, et al., "Transduction of Human CD34+ Cells that Mediate Long-Term Engraftment of NOD/SCID Mice by HIV Vectors," *Science*, 1999, pp. 682-686, vol. 283.

Miyoshi, et al., "Stable and Efficient Gene Transfer into the Retina Using an HIV-Based Lentiviral Vector," *Proc. Natl. Acad. Sci.*, 1997, pp. 10319-10323, vol. 94.

Naldini, et al., *Science*, 1996, pp. 263-267, vol. 272.

Naldini, et al., "Efficient Transfer, Integration, and Sustained Long-Term Expression of the Transgene in Adult Rat Brains Injected with a Lentiviral Vector," *Proc. Natl. Acad. Sci.*, 1996, pp. 11382-11388, vol. 93.

Natsoulis and Boeke,"New Antiviral Strategy using Capsid-Nuclease Fusion Proteins," *Nature*, 1991, pp. 632-635, vol. 352.

Natsoulis, et al., "Targeting of a Nuclease to Murine Leukemia Virus Capsids Inhibits Viral Multiplication," *Proc. Nat. Acad. Sci USA*, 1995, pp. 364-367, vol. 92.

Ogawa, et al., "Mutational Analysis of the Human Immunodeficiency Virus vpr Open Reading Frame," *J. Virol.*, 1989, pp. 4110-4114, vol. 63(9).

Orkin, et al., "Report and Recommendations of the Panel to Assess the NIH Investment in Research on Gene Therapy," 1995, *NIH Panel Report*, entire report.

Park, et al., "Amino Acid Sequence Requirements for the Incorporation of the Vpx Protein of Simian Immunodeficiency Virus into Virion Particles," *J. Acq. Immune Def. Synd.*, 1995, pp. 506-510, vol. 10.

Park, et al., "Targeting a Foreign Protein into Virion Particles by Fusion with the Vpx Protein of Simian Immunodeficiency Virus," *J. Acq. Immunoe Def. Synd.*, 1996, pp. 341-350, vol. 11.

Paxton, et al., "Incorporation of the Vpr into Human Immunodeficiency Virus Type 1 Virions: Requirement for the p6 Region of gag and Mutational Analysis," J. Virol., 1993, pp. 7229-7237, vol. 67.

Percy, et al., "A poliovirus Replicon Containing the Chloramphenicol Acetyltransferase Gene Can Be Used to Study the Replication and Encapsidation for Poliovirus RNA," *J. Virol*, 1992, pp. 5040-5046.

Re, et al., "Human Immunodeficiency Virus Type 1 Vpr Arrests the Cell Cycle in G2 by Inhibiting the Activation of p34cdc2-Cyclin B," *J. Virol.*, 1995, pp. 6859-6864, vol. 69(11).

Rogel, et al., The Human Immunodeficiency Virus Type 1 vpr Gene prevents Cell Proliferation During Chronic Infection, *J. Virol.*, 1995, pp. 882-888, vol. 69(2).

Sato, et al., Targeting of a Chrolamphenicol Acetyltransferase to Human Immunodeficiency Virus Particles Via Vpr and Vpx, *Microbiol. Immunol.*, 1995, pp. 1015-1019, vol. 39(12).

Schnell, et al., "Construction of a Novel Virus That Targets HIV-1 Infected Cells and Controls HIV-1 Infection," *Cell Press*, 1997, pp. 849-857, vol. 90.

Shibata, et al., "Construction and Characterization of an Infectious DNA Clone and of Mutants of Simian Immunodeficiency Virus Isolated from the African Green Money," *J. Virol.*, 1990, pp. 307-312, vol. 64(1).

Shibata, et al., "Generation of a Chimeric Human and Simain Immunodeficiency Virus Infectious to Monkey Peripheral Blood Mononuclear Cells," *J. Virol.*, 1991, pp. 3514-3520, vol. 65(7).

Shibata, et al.,"Mutational Analysis of the Human Immunodeficiency Virus Type 2 (HIV-2) Genome in Relation to HIV-1 and Simian Immunodeficiency Virus SIVabm," *J. Virol.*, 1990, pp. 742-747, vol. 64.

Schuman, et al., Therapeutic Effect of Gag-Nuclease Fusion Protein on Retrovirus-Infected Cell Cultures, *J. Virol.*, 1996, pp. 4329-4337, vol. 70.

Smith, et al., Single-Step Purification of Polypeptides Expressed in *Escherichia coli* as Fusions with Glutathione S-Transferase, *Gene*, pp. 31-40, vol. 67.

Stewart, et al., "Human Immunodeficiency Virus Type 1 VPR Induces Apoptosis Following Cell Cycle Arrest," *J. Virol*, 1997, pp. 5579-5592, vol. 71.

Tristem, et al., "Evolution of the Primate Lentiviruses: Evidence from Vpx and Vpr," *EMBOL J.*, 1992, pp. 3405-3412, vol. 11.

Tristem, et al., "Origin of Vpx in Lentiviruses," *Nature*, 1990, pp. 341-342, vol. 347.

Trono, et al., "HIV Accessory Proteins" Leading Roles for the Supporting Cast, *Cell*, 1995, pp. 189-192, vol. 82.

Verhasselt, et al., "Retrovirally Transduced CD34++ Human Cord Blood Cells Generate T Cells Expressing High Levels of the Retroviral Encoded Green Fluorescent Protein Marker In Vitro," *Blood*, 1998, pp. 431-440, vol. 91.

Wakefield, J.K., et al., "Destroying HIV from Within," Fourth Conference on Retroviruses and Opportunistic Infections, Jan. 22, 1997.

Wang, et al., "Particles Assembly and Vpr Expression in Human Immunodeficiency Virus Type 1 -Infected Cells Demonstrated by Immunoelectron Microscopy," 1994, pp. 2607-2614, vol. 75.

Westervelt, et al., Dual Regulation of Silent and Productive infection in Monocytes by Distinct Human Immunodeficiency Virus Type 1 Determinants, *J. Virol.*, 1992, pp. 3925-3931, vol. 66(6).

Wong-Staal, et al., "Human Immunodeficiency Virus: The Eighth Gene," *Aids Research and Human Retroviruses*, 1987, vol. 3(1).

Wu, et al., "Functional RT and IN Incorporated Into HIV-1 Particles Independent of the Gag/Pol Precursor Protein," *J. Virol.*, 1994, pp. 6161-6169, vol. 68.

Wu, et al., "Functional RT and IN Incorporated Into HIV-1 Particles Independent of the Gag/Pol Precursor Protein," *EMBO J.*, 1997, pp. 5113-5122, vol. 16.

Wu, et al., "Functional RT and IN Incorporated Into HIV-1 Particles Independent of the Gag/Pol Precursor Protein," *EMBO J.*, 1997, pp. 101-109, vol. 16.

Wu, et al., "HIV/SIV Virion Associates Accessory Genes Mediate Efficient Packaging of Nuclease Fusion Proteins Into the Virus Particle," *The First National Conference of Human Retroviruses and Related Infections*, 1993, Washington, D.C.

Wu, et al., "Inhibition of HIV-1 Replication by Targeting Vpr Fusion Proteins to Virions," *Biol. Abstr./BBM*, 1995, p. 323, vol. 47(4).

Wu, et al., Inhibition of Human and Simian Immunodeficiency Virus Protease Function by Targeting Vpx-Protease-Mutant Fusion Protein Into Viral Particles, *J. Virol.*, 1996, pp. 3378-3384.

Wu, et al., "Localization of the Vps Packaging Signal within the C Terminus of the Human Immunodeficiency Virus Type 2 Gag Precursor Protein," *J. Virol.*, 1994, pp. 6164-6169, vol. 68(10).

Wu, et al., "Multiple Glycoproteins Synthesized by the Smallest RNA Segment (S10) of Bluetongue Virus," J. Virol., 1992, pp. 7104-7112, vol. 66.

Wu, et al., Targeting Foreign Proteins to Human Immunodeficiency Virus Particles Via Fusion with Vpr and Vpx, J. Virology, 1995, pp. 3389-3398, vol. 69. (revised manuscript, #JV1 1529-94).

Wu, et al., "Targeting Foreign Proteins to Human Immunodeficiency Virus Types 1 and 2 Via Fusion with Vpr and Vpx," Biol. Abstr./RRM, 1995, vol. 47. (MT-323).

Wu, X., et al., "Incorporation of Functional RT Protein into HIV-1 Particles by Trans Expression as a VPR-RT Fusion Protein," $36^{th}$ Interscience Conference on Antimicrobial Agents and Chemotherapy, Sep. 22, 1997.

Wu, X., et al., "Infectious Human Immunodeficiency Virus Type I Derived From Reverse Transcriptase (RT) and Integrase (IN) Minus Provirus Complemented With RT and IN Trans," Cold Spring Harbor Conference on Retroviruses, May 20, 1997.

Wu, X., et al., "HIV-1 DNA Synthesis in Infected Cells Requires IN Protein," Cold Spring Harbor Conference on Retroviruses, May 20, 1997.

Wu, X., et al., "Virion Incorporation of Vpr-RT Fusion Protein Rescues Replication of RT-Defective-HIV-1," Third Conference on Retroviruses and Opportunistic Infections, Jan. 28, 1996.

Wu, X., et al., "Virion Incorporation of VPR-RT Fusion Protein Rescues Replication of RT-Defective-HIV-1," Cold Spring Harbor Conference on retroviruses, May 21, 1996.

Yao, et al., "Mutagenic Analysis of Human Immunodeficiency Virus Encodes a Virion-Associated Protein," J. Virol., 1990, pp. 5688-5693, vol. 64(11).

Yu, et al., "Open Reading Frame vpr of Simian Immunodeficiency Virus Facilitates Efficient Viral Replication in Fresh Lymphocytes and Macrophages," J. Virol., 1991, pp. 5088-5091, vol. 65(9).

Yu, et al., Vpx of Simian Immunodeficiency Virus is Localized Primarily Outside the Virus Core in Mature Virions, J. Virol., 1993, pp. 4386-4390, vol. 67(7).

Yuan, et al., "Human Immunodeficiency Virus vpr Gene Encodes a Virion-Associates Protein," AIDS Research and Human Retroviruses, 1990, pp. 1265-1271, vol. 6(11).

Zhang, et al., Rate and Mechanism of Nonhomologous Recombination During a Single Cycle of Retroviral Replication, Science, 1993, pp. 234-238, vol. 259.

Zhao, et al., "Biochem. Mechanism of HIV-1 Vpr Function," J. Biol. Chem., 1994, pp. 15577-15582, vol. 269.

Zhao, et al., Biochemical Mechanism of HIV-1 Vpr Function: Oligomerization Mediated by the N-Terminal Domain, J. Biol. Chem., 1994, pp. 32131-32137, vol. 269.

Zufferey, Woodchuck Hepatitis Virus Posttranscriptional Regulatory Element Enhances Expression of Transgenes Delivered by Retroviral Vectors, J. Virol., 1999, pp. 2886-2892, vol. 73.

Kobinger, G.P., et al., "Virion-Targeted Viral Inactivation of Human Immunodeficiency Viris Type 1 by Using Vpr Fusion Proteins," Journal of Virology, 1998, pp. 5441-5448, vol. 72(7).

Mochizuki, H., et al., "High-Titer Human Immunodeficiency Virus Type 1-Based Vector Systems for Gene Delivery into Nondividing Cells," Journal of Virology, 1998, pp. 8873-8883, vol. 72(11).

Weldon, R.A., et al., "Incorporatin of Chimeric Gag Protein into Retroviral Particles," Journal of Virology, 1990, pp. 4169-4179, vol. 64(9).

Banerjee, S., et al., "Reverse transcriptase activity in bovine marrow: purification of a 66-kDa enzyme," Biochimica et Biophysica Acta, 2000, pp. 1-5, vol. 1480.

Bennett, P.M., "Integrons and gene cassettes: a genetic construction kit for bacteria," Journal of Antimicrobial Chemotherapy, 1999, pp. 1-4, vol. 43.

Daboussi, M.J., "Fungal transposable elements and genome evolution," Genetica, 1997, pp. 253-260, vol. 100.

Fletcher, T.M., et al., "Targeting Deleterious Enzymes to HIV/SIV Virions," Jan. 29, 1995, The Second National Conference on Human Retroviruses and Related Infections, ABST.
Groth, A.C. and Calos, M.P., "Phage integrase: Biology and Applications," *J. Mol. Biol.*, 2004, pp. 667-678, vol. 335.
Kempken, F. and Kück, U., "Transposons in filamentous fungi-facts and perspectives," *BioEssays*, 1998, pp. 652-659, vol. 20.
Yu, X., et al., "Mutations of Human Immunodeficiency Virus Type 1 $p6^{Gag}$ Domain Result in Reduced Retention of Pol Proteins during Virus Assembly," *Journal of Virology*, 1998, pp. 3412-3417, vol. April.
Zhu, K., et al., "Requirements for Integrase during Reverse Transcription of Human Immunodeficiency Virus Type 1 and the Effect of Cysteine Mutations of Integrase on Its Interactions with Reverse Transcriptase," *Journal of Virology*, 2004, pp. 5045-5055, vol. May.

* cited by examiner

TRANS-LENTIVIRAL VECTOR PARTICLES AND TRANSDUCTION OF EUKARYOTIC CELLS THEREWITH

CROSS-REFERENCE TO RELATED APPLICATIONS

This application is a continuation application of U.S. patent application Ser. No. 09/709,751, filed Nov. 10, 2000 now abandoned, which is a continuation-in-part of U.S. patent application Ser. No. 09/460,548, filed Dec. 14, 1999 now U.S. Pat. No. 6,555,342, which is a continuation-in-part of U.S. patent application Ser. No. 09/089,900, filed Jun. 3, 1998 (abandoned). U.S. patent application Ser. No, 09/709,751 further claims priority to U.S. Provisional Application No. 60/164,626, filed Nov. 10, 1999. Each of these applications is herein incorporated by reference in their entirety including all drawings.

BACKGROUND OF THE INVENTION

The following description includes information that may be useful in understanding the present invention. It is not an admission that any of the information provided herein is prior art, or relevant, to the presently claimed inventions, or that any publication specifically or implicitly referenced is prior art.

This application relates to retroviral vectors, particularly trans-lentiviral vectors, for the efficient and stable transduction of cells with heterologous nucleic acid sequences.

Lentiviral vectors are able to transduce nondividing as well as dividing cells and sustain expression of heterologous nucleic acid sequences in several target tissues in vivo, including brain, liver, muscle, and hematopoietic stem cells. Miyoshi et al. (1999) *Science* 283:682-686; Kafri et al. (1997) *Nature Genetics* 17:314-31; Akkina et al. (1996) *J. Virol.* 70: 2581-2585; Naldini et al. (1996) *Science* 272:263-267. Lentiviral vectors therefore hold great promise for gene therapy, and clinical trials to evaluate their safety and efficacy for treating certain human diseases are being considered. Amado et al. (1999) *Science* 285:674-676. However, and despite this promise, there remains a concern for safety insofar as lentiviruses are known to cause disease.

To address this, so-called "split-function" vector systems have been designed that express the essential lentiviral genes (gag, pol, and env) on separate genetic elements. Naldini et al., supra; Kafri et al. (1999) *J. Virol.* 73:576-84; Wu et al. (1997) *EMBO,* 16(16):5113-5122. The in trans "piecemeal" supply of these coding elements to a packaging cell allows for the production of infectious viral particles having the ability to transduce cells, but otherwise having a reduced potential for genetic recombination and the establishment of new infection, i.e., integrated recombinant proviral DNA. Still, the possibility exists that replication competent retroviruses (RCRs) and accompanying pathology can result from genetic recombination.

There is thus a continuing need for improved lentiviral vector systems that afford relatively high vector particle production, improved transduction capabilities, and which have even lower potential for RCR events.

SUMMARY OF THE INVENTION

The invention features improved lentiviral and trans-lentiviral vector systems and methods for delivering heterologous nucleic acid sequences to cells with greater efficiency and/or effect.

In a first aspect, the invention features a trans-lentiviral vector system for transducing nondividing cells. Examples of such nondividing cells would include, but would not be limited to, CD34+ cells, stem cells, macrophages, hepatocytes, neurons, myocytes, cells of the eye, and somatic cells.

The term "trans-lentiviral vector system" as used herein contrasts with a "lentiviral vector system." While both systems are typically "split function" and possess env, packaging, and gene transfer (vector) nucleic acid constructs as those terms are known in the art (see, e.g., FIG. 2 for an illustrative embodiment of a lentiviral vector system), a trans-lentiviral vector system is distinguishable in that its RT and IN functions are supplied in trans from at least one vector other than the packaging construct. In such a system, the packaging construct preferably retains a functional gag sequence, but otherwise contains a nonfunctional, altered, or compromised ability to form a functional gag-pro-rt-in (together "gag-pol") fusion product (see, e.g., FIG. 1). At least one of these genes is disrupted, interrupted, missing in whole or in part, or otherwise nonfunctional such that it cannot appropriately produce its specific gene or fusion product or otherwise promote efficient packaging and/or infection. The purpose is to further "split", disarm, prevent, and/or minimize the possibility for formation of a wild-type or replication competent retrovirus (RCR). Such a system also enables the vector stocks produced therefrom to be monitored for a defect as a further means to eliminate the generation of RCR.

Thus, in a trans-lentiviral system an additional complementation or supply of a deficient gene or gene product, e.g., via another vector of the system, or else in a packaging or intermediate cell line in which the vector system is used for producing infectious trans-lentiviral particles, is required. A nonlimiting illustration of this is provided in a comparison of FIGS. 1 and 2. FIG. 2 demonstrates one embodiment of a lentiviral vector system. In this system, the packaging construct contains gag, pro, rt, and in genes that are all functional (boxed), e.g., resembling a wild-type HIV lentiviral configuration. FIG. 1, by contrast, depicts one possible embodiment of a trans-lentiviral packaging system in which only gag and pro are boxed on the packaging construct (signifying functionality) and wherein RT and IN remain unboxed (signifying lack of function or presence) on the packaging construct, but which are functionally contained on another construct. Complementing RT and IN gene(s) or gene product(s) therefore derive from another genetic element of the system, e.g., a "trans-enzyme construct" as shown in FIG. 1. This particular trans-lentiviral system, and variations of it, are discussed in greater detail in U.S. patent application Ser. No. 09/460,548, PCT patent application US00/18597, and in Wu et al. (1997) *EMBO* 16(16):5113-5122.

A "gene transfer vector" as described herein is a nucleic acid sequence that is typically used in conjunction with other lentiviral or trans-lentiviral vector system vectors to produce vector particles, e.g., so that the particles can then transduce a target cell of interest. A gene transfer vector preferably contains elements that promote mRNA production and packaging into vector particle, e.g., a shine-delga. The gene transfer vector also preferably contains sequences necessary for reverse transcription, e.g., a primer binding site (PBS) or equivalent, a polypurine tract (PPT), a central terminator sequence (CTS), and other sequences, e.g., a Rev responsive element (RRE), and long terminal repeats (LTRs) or portions thereof that can promote reverse transcription and integration into a host genome. Preferably such vector also includes a heterologous nucleic acid sequence of interest that is used to promote a given phenotype or genotype within a cell to be transduced. Alternatively, the vector can be supplied without such a sequence present, but contain a site or sites for ready inclusion of such a heterologous nucleic acid sequence of interest, e.g., by supplying the vector with a convenient restriction enzyme site or sites for positioning such a sequence therein. The gene transfer vector may further and preferably does contain one or more sequences that act in concert with a heterologous nucleic acid of interest, e.g., genetic regulatory elements such as promoters, terminators, enhancers, WPRE stabilizing sequences, etc.

A "heterologous nucleic acid sequence of interest" means a sequence that is introduced from outside the host cell for effect within the host cell. It can have any level of homology with a native or existing sequence within the host cell. In preferred embodiments, this sequence is a gene or portion thereof (e.g., a coding sequence) that is capable of transcription and/or translation within an infected or transduced cell. In some embodiments, this sequence may be accompanied by regulatory elements well known in the art such as described above. These elements can help, e.g., to express, suppress, stabilize, and/or tag the introduced sequence and/or resulting gene product. Examples of such elements are promoters, enhancers, inducible elements, introns, post-transcriptional regulatory elements such as WPRE, and/or affinity tags for purification or labeling (e.g., with antibodies), etc. Preferred coding sequences include marker or reporter genes, e.g., luciferase, Bgal, GFP, antibiotic resistance genes, and/or therapeutic genes. One of skill will appreciate that numerous possibilities exist.

Thus, in another aspect the invention features a gene transfer vector as described above for use in a trans-lentiviral vector system. Optionally, and advantageously, the gene transfer vector preferably includes one or more sequences selected from woodchuck hepatitus virus posttranscriptional regulatory element (WPRE) and PPT-CTS, or functional equivalents thereof to help promote enhanced titer of vector particles and transduction efficiency. In particularly preferred embodiments, the gene transfer vector contains both a WPRE and a PPT-CTS sequence.

In another aspect, the invention features a trans-lentiviral vector particle produced using the gene transfer vector of the first aspect. A trans-lentiviral vector particle is a proteinaceous, capsid-like virion that is produced by expression of gag, pro, rt, in, and env retroviral genetic elements in a host cell. The particle produced preferably further contains an internal mRNA equivalent of the gene transfer vector and is infectious, or can be made infectious, for a given cell type to be transduced.

A further aspect of the invention features a cell transduced using a trans-lentiviral vector particle and gene transfer vector according to the preceding aspects of the invention. Preferably the cell is a primary non-dividing cell, preferably one selected from macrophages and CD34+ cells, and most preferably CD34+ cells.

In another aspect, the invention features a method of transducing a cell using a trans-lentiviral vector system and gene transfer vector according to the preceding aspects. The method includes providing or forming a trans-lentiviral vector particle from a trans-lentiviral vector system and then transducing a cell with that vector particle. The method for forming a trans-lentiviral vector particle may include first transfecting a packaging cell line with the different genetic elements or constructs of a trans-lentiviral vector system. These formed particles are then harvested away from the packaging cell and used to transduce a cell of interest. Any of the specific embodiments included for the preceding aspects of the invention may also be incorporated into this aspect. In preferred embodiments, the transduced cell is then assayed or observed for a phenotype or genotype indicative of the transduction.

For each of the above aspects and embodiments, a further preferred embodiment is that the trans-lentiviral vector system contains one or more HIV genetic elements, preferably HIV-1 genetic elements. Preferably the host cells infected or transduced are animal cells, more preferably vertebrate, more preferably still mammalian, and most preferably human. However, one of ordinary skill will appreciate that the invention is suitable, depending on the particular context, for use with many different lentiviral elements from many different lentiviral viruses, including those that infect species of organisms other than humans. What is necessary is that the elements function together to produce an infectious particle capable of infecting a cell of interest from an organism of interest. One of ordinary skill in the art can determine various successful combinations of lentiviral elements and host cells without undue experimentation.

In certain preferred embodiments of the invention, the gene transfer vector includes the specific regulatory elements, Woodchuck Hepatitus Virus Postranscriptional Regulatory Element ("WPRE") and/or a polypurine tract-central terminator sequence ("PPT-CTS"). These elements have been shown to be highly conserved and to respectively enhance gene expression (Zufferey et al. (1999) *J. Virology* 73(4): 2886-2892 and vector particle titer (Charneau et al. (1994) *J. Mol. Biol.* 241:651-662; Charneau et al. (1992)*J. Virology* 66(5):2814-2820; Zennou et al. (2000) *Cell* 101:173-185) when used in conjunction with traditional lentiviral vector systems. No data has yet been generated, however, using trans-lentiviral vector system of the invention.

Given the complexity of retroviral biology that requires fusion protein folding within the lentiviral vector particle, prior to the invention it was unobvious that a trans-system would work where the retroviral Gag-pol gene components are not all expressed in the same fusion protein product, but rather are complemented in trans by the supply of the components on separate genetic vectors. The Applicants show here that, not only does the trans-lentiviral vector system work, but that incorporating the ppt-cts sequence into the gene transfer vector of such a system improves the titer from about three to about five fold (e.g., in one instance from about $4.5 \times 10^5$ to about $1.5 \times 10^6$ particles/ml). This enhanced titer is very useful, especially for the trans-lentiviral system, which affords greater theoretical safety value, but which otherwise produces a much lower titer.

The WPRE sequence functions differently than the PPT-CTS. Whereas the latter is thought to promote reverse transcription and nuclear import, the former is thought to stabilize transcripts and therefore result in increased translation and product signal. The Applicants have observed a cumulative effect of these two sequences when operatively positioned within the same gene transfer vector, regardless of whether used in a lentiviral or translentiviral system. Functional variations of these two sequences, or functional analogs of these sequences, are also anticipated to exist or to be producible without undue experimentation, and to have merit with the invention. By including these sequences (cts-ppt and WPRE) in the lenti- and trans-lentiviral vector systems, the titer, transduction efficiency, and thus utility for transducing cells is enhanced, especially for non-dividing cells, such as muscle, neurons, stem cells, unstimulated CD34+ cells, airway cells, liver cells, cells of the eye, and other somatic cells. Non-dividing cells may be defined as somatic cells, cells with a limited life span, or primary cells that divide slowly. However, such cells may also be stimulated to divide more rapidly, e.g., in the instance of CD34+ bone marrow cells, i.e., pluripotent hematopoietic stem cells.

For example, the core sequence, SEQ ID NO: 1 (corresponding to nucleotides 1093 to 1684 of GenBank accession # J04514), represents one embodiment of a WPRE sequence, but it is anticipated, e.g., that by substituting, removing, or inserting one or more bases into this core sequence and testing resulting effect, one of ordinary skill will be able to identify derivative sequences with similar, lesser, or perhaps even better utility for use with the invention.

Similarly, the core sequence 5' AAAAGAAAAGGGGG-GATTGGGGGGTACAG TGCAGGGGAAAGAATAGTA-GACATAATAGCAACAGACATACAAACTAAAGA ACTACAAAAACAAATTACAAAAATTCAAAATTTT3' (SEQ ID NO:2) represents one preferred embodiment of a nucleic acid sequence containing the PPT-CTS. This sequence derives from an HIV isolate described by Ghosh et al. (1993) *Virology* 194:858. However, it will be appreciated that, although this particular tract is highly conserved among the lentiviruses, natural variations exist for the different HIV isolates and different lentiviral species, which can likely be substituted in. See, e.g., Zennou et al. (2000) *Cell* 101:173 (describing different HIV isolate); Stetor et al. (1999) *Biochemistry* 38:3656-3667 (describing equine infectious anemeia virus tract ("EIAV"). Further, it is anticipated that man-made variations of these sequences (see, e.g., Hunges et al. (1992) Virology 190:440-442) exist and/or can be identified by those of ordinary skill using routine experimentation. Preferably a variant PPT and/or CTS sequence attached thereto will substantially preserve the PPT base sequence, 5'AAAA-GAAAAGGGGGG3' (SEQ ID NO:3), e.g., by preserving or retaining at least 5, preferably at least 9, and more preferably at least 11 consecutive purines. Further, the CTS sequence must also be substantially preserved and is characterized predominantly by sequences, such as poly A and/or poly T tracts, that promote a "flap" characteristic or similar to those typical of retroviral nuclear import features.

Advantages of the invention therefore include the supply and use of lentiviral and trans-lentiviral gene transfer vectors that afford superior qualities, e.g., the ability to generate high titer vector particle stocks and/or the ability to transduce cells more efficiently, particularly primary non-dividing cells, while maintaining and/or improving safety.

Other advantages, aspects, and embodiments will be apparent from the figures, the detailed description, and the claims.

DETAILED DESCRIPTION OF THE PREFERRED EMBODIMENTS

Figure 2:
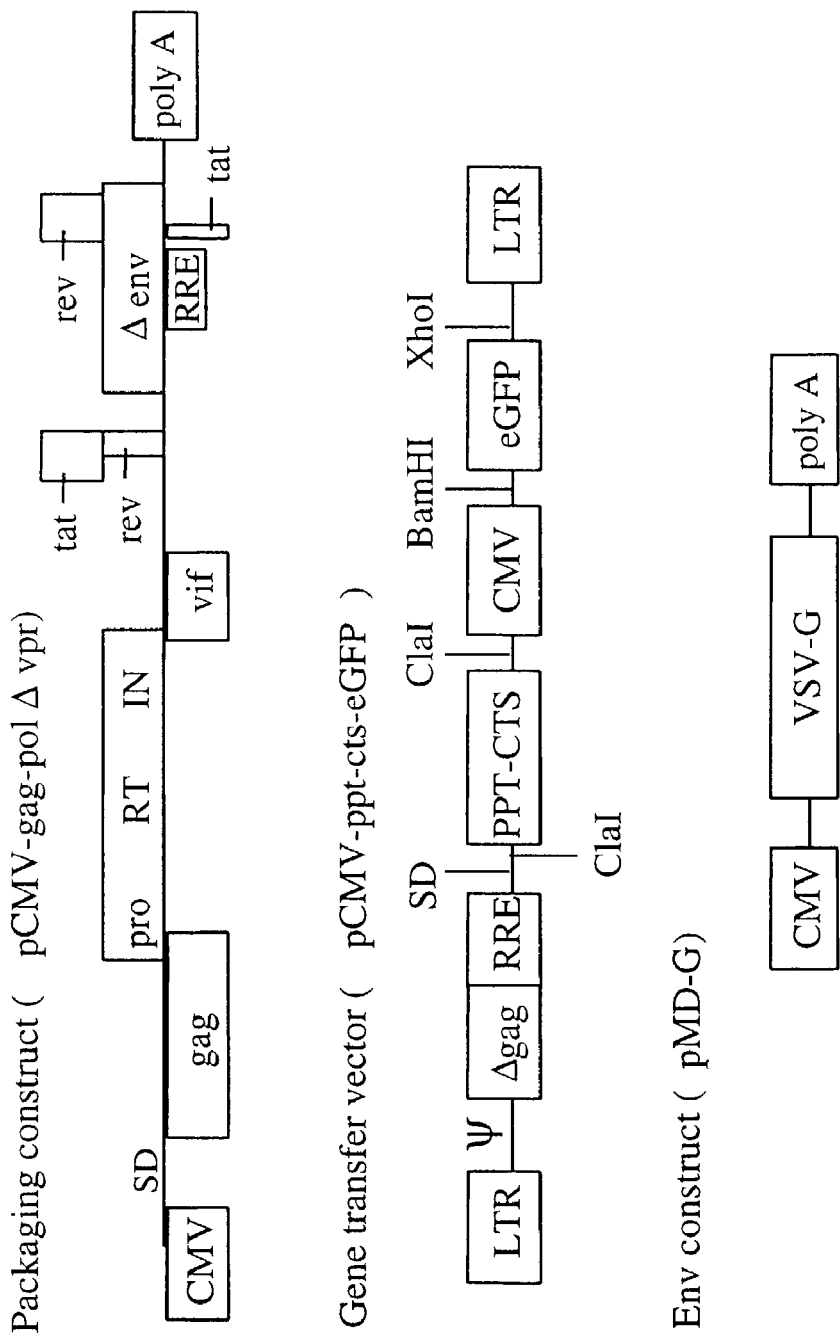
FIG. 2 is a schematic illustrating a more traditional split-function lentiviral vector system containing all four functional retroviral genes, gag, pro, rt, and in, on the same packaging construct, with no trans-enzyme construct.

The basic components of current retroviral-based gene delivery systems include packaging, gene transfer, and envelope elements that are usually supplied on separate genetic constructs to promote safety (see, e.g., FIG. 2). The packaging construct encodes the structural (gag) and catalytic (po) proteins that are necessary to generate an infectious particle. The vector construct (or "gene transfer vector") typically contains the genetic material of interest that is to be transferred into the target cell, along with a packaging signal ($\psi$), a promoter for gene expression, and various other cis-acting sequences necessary for reverse transcription and integration, e.g., long terminal repeats (LTRs) or SIN equivalents, primer binding sites (pbs), etc. The envelope (env) component is usually also supplied on a separate "env construct" and mediates recognition and entry of the virus into the target cell. Typically, and for ease and breadth of use, a heterologous env protein such as the G protein from vesicular stomatitis virus (VSV-G) is employed. See, e.g., Akkina et al. (1996) *J. Virology* 70(4):2581-2585.

Figure 1:
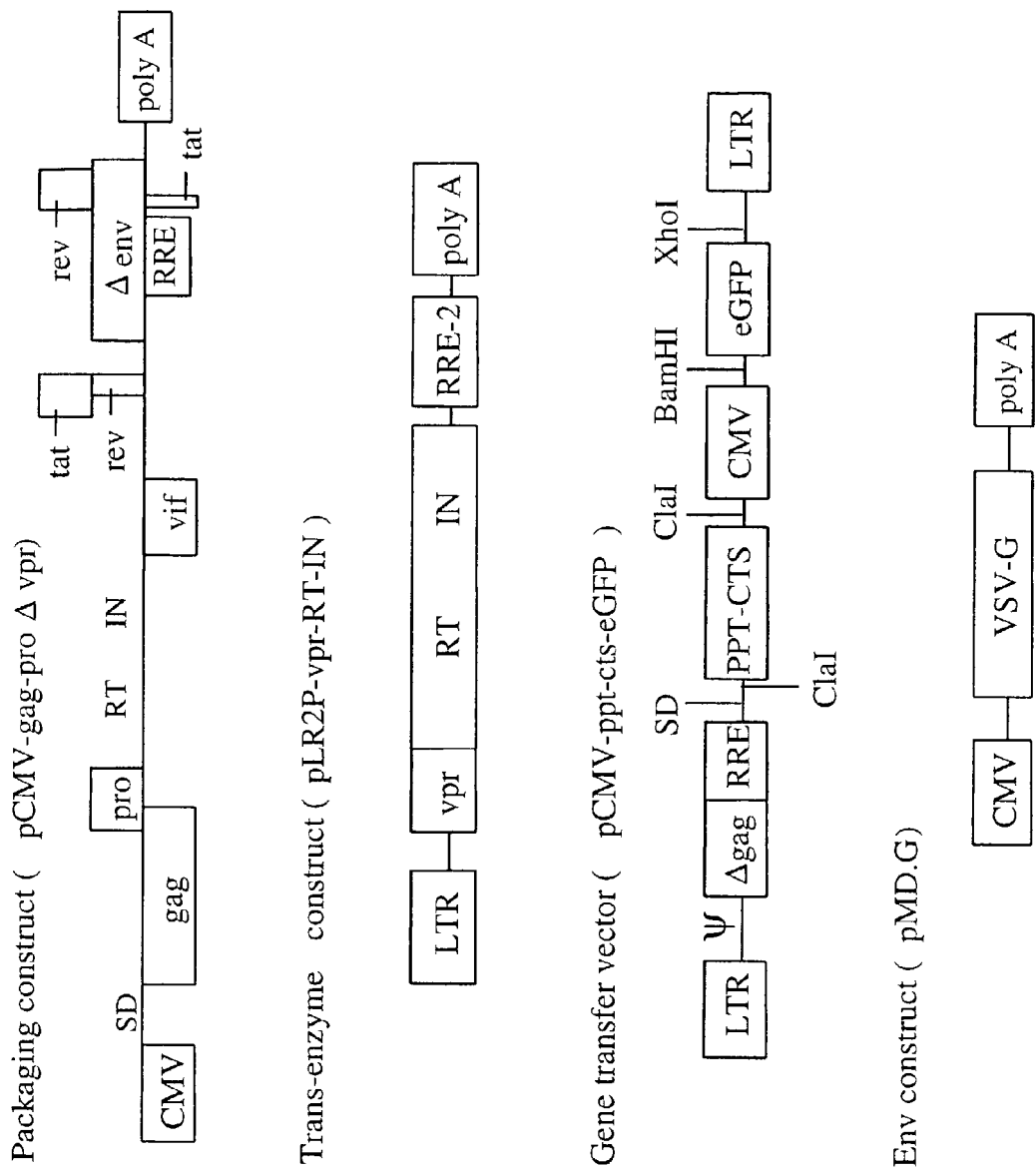
FIG. 1 is a schematic illustrating one embodiment of a trans-lentiviral vector system according to the invention. Note the inclusion of the PPT-CTS tract in the gene transfer vector, the trans-enzyme construct harboring the reverse transcriptase and integrase retroviral genes, and the inactive (unboxed) RT and IN sequences in the packaging construct.

We previously described the system of FIG. 1 to represent a safety improvement over the system of FIG. 2 in that it splits essential genes that are highly conserved as components of gag-pol, thus making more improbable their ability to recombine into RCRs. In the embodiment of FIG. 1, a fourth construct, the "trans-enzyme" element, contains the retroviral genes reverse transcriptase and integrase apart from their native configuration. Of significance, the packaging construct in the translentiviral vector system now consists of gag-pro wherein RT-IN have been deleted. See, e.g., U.S. patent application Ser. No. 09/460,548, and Wu et al. (1997) *EMBO* 16(16):5113-5122. This particular system utilizes the HIV accessory protein, Vpr, as a vehicle to deliver other proteins into HIV particles by expression in trans as a heterologous fusion protein. See Wu et al. (1995) *J. Virol.* 69:3389-3398; see also copending U.S. patent application Ser. Nos. 08/947, 516 and 09/089,900, herein incorporated by reference.

We herein describe a further utility of the trans-lentiviral vector system in the transduction of primary non-dividing cells and improvements through the use of cis-acting CTS-PPT sequences (Zennou et al. *Cell* 101: 173-185; Charneau et al. *J. Mol. Biol.* 241:651-662) and/or WPRE sequences (Zufferey et al. (1999) *J. Virology* 73:2886) in the gene transfer vector. These sequences, singularly and cumulatively, result in greater transduction efficiencies and/or vector particle titer relative to that achieved using the same vectors lacking such sequences, particularly in primary non-dividing cells.

EXPERIMENTAL

Example 1

Comparison of Translentiviral and Lentiviral Vector Systems

We compared transduction efficiency using lentiviral-versus translentiviral-derived vector particles. For the latter, RT and IN were provided in trans, 293T cells were transfected with the pCMV-gag-pro Δvpr packaging plasmid, the pLR2P-vpr-RT-IN trans-enzyme plasmid, the pMD.G env plasmid, and the pCMV-eGFP vector plasmid to produce trans-lentiviral vector particles. Using optimal transfection conditions, the titer of the trans-lentiviral vector in HeLa cells was reproducibly 3-5-fold less than that the corresponding lentiviral vector.

Two possibilities were considered to explain the difference. First, without the PPT and the CTS, which have been shown to be involved in HIV-1 reverse transcription (Charneau et al. (1994) *J. Mol. Biol.* 241:651-662), the splitting of RT-IN from gag-pol may effect the efficiency of reverse transcription. Second, the transfection of four plasmids to generate trans-lentiviral vector particles is less efficient than the three-plasmid transfection used to produce lentiviral vector particles.

Example 2

Improving Transduction Efficiencies Through Incorporation of CTS and PPT Sequences We introduced sequences containing the central terminator sequence (CTS) and central polypurine tract (PPT) into the gene transfer vector of each of the lenti and trans-lentiviral vector systems. PPT and CTS have been implicated in HIV-1 reverse transcription success (Charneau et al. (1994) *J. Mol. Biol.* 241:651-662) and, more recently, in nuclear import of viral sequences. Zennou et al. (2000) *Cell* 101: 173-185. The result was that the titer of the trans-lentiviral vector (of FIG. 1) in HeLa cells increased 3 to 5-fold, up to $1.5 \times 10^6$ CFU/ml as shown in Table 1.

TABLE I

CTS-ppt sequences increase vector titer

| packaging system | gene transfer vector | |
|---|---|---|
| | without CTS-PPT | with CTS-PPT |
| trans-lentiviral | $2\text{-}3 \times 10^5$ | $0.8\text{-}1.5 \times 10^6$ |
| lentiviral | $4\text{-}8 \times 10^5$ | $3\text{-}6 \times 10^6$ |

The titer of lentiviral vector similarly increased, up to $6 \times 10^6$ CFU/ml. The titer of the FIG. 1 trans-lentiviral vector reached $10^8$ CFU/ml by a single concentration step, indicating that the particles are stable after being subjected to ultracentrifugation.

To construct the pCMV-PPT-CTS-eGFP plasmid, a 150 bp sequence of DNA (coordinates 4327 to 4483) containing the central polypurine tract (PPT) and central terminal site (CTS) was PCR amplified from the HIV-1 pSG3 molecular code (Ghosh et al. (1993) *Virol.* 194:858-864) and ligated into the unique ClaI site of pHR-CMV-eGFP.

Example 3

Figure 3:
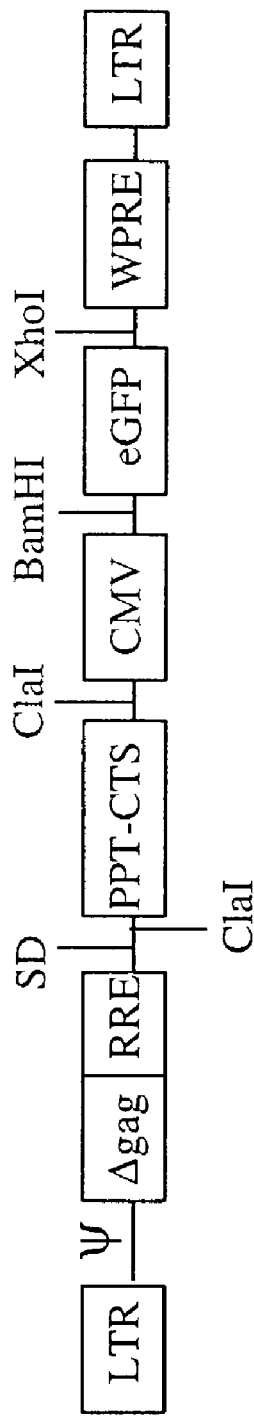
FIG. 3 is a schematic illustrating a gene transfer vector construct embodiment that includes each of the PPT-CTS and WPRE sequences.
Figure 4:
FIG. 4B is a fluorescence micrograph of terminally differentiated macrophages which were transduced with the lentiviral vector derived from the genetic elements depicted in FIG. 2, except that the gene transfer vector of FIG. 3 was substituted for that shown in FIG. 2.
FIG. 4A is a fluorescence micrograph of terminally differentiated macrophages which were transduced with the trans-lentiviral vector derived from the genetic elements depicted in FIG. 1, except that the gene transfer vector of FIG. 3 was substituted for that shown in FIG. 1.
Figure 4:
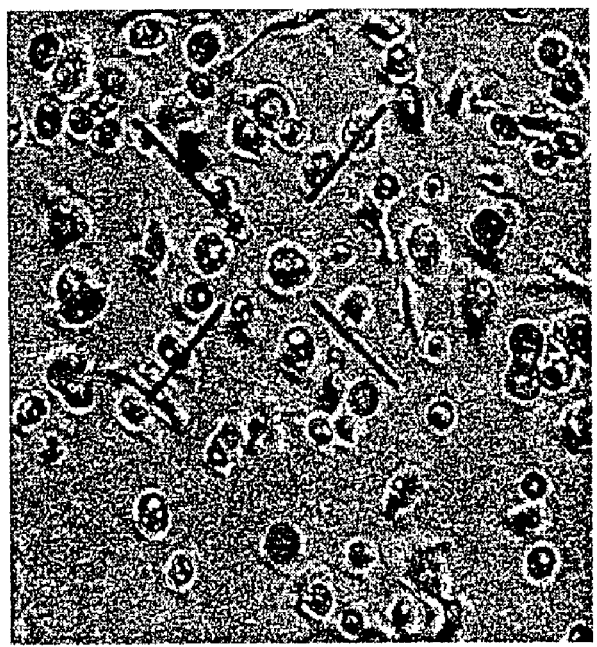
Figure 7:
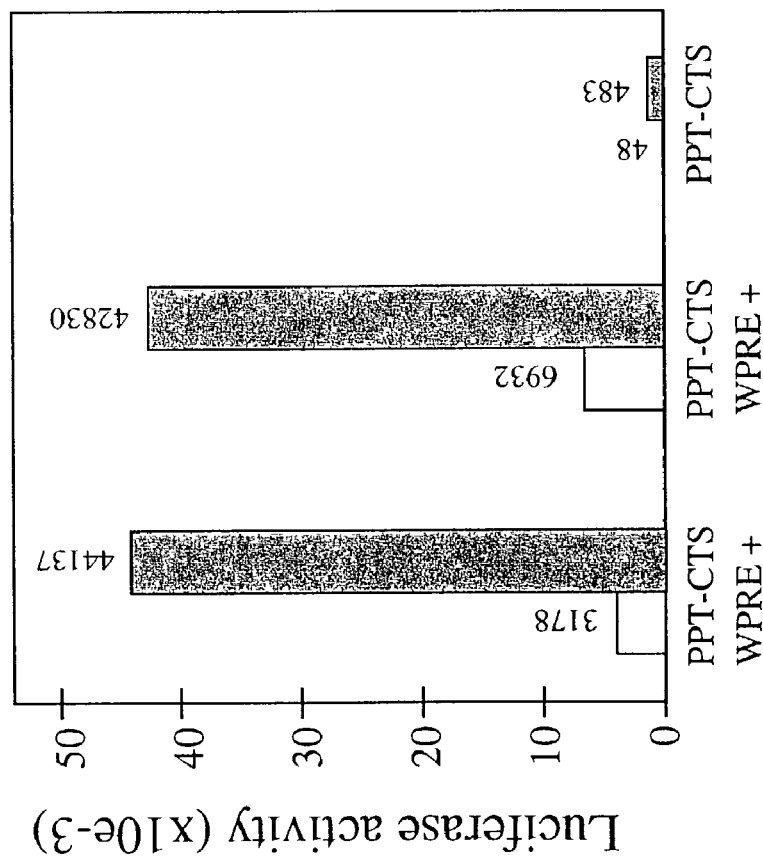
FIG. 7 shows transduction of cells in the airway of mice using a gene transfer vector as depicted in FIG. 1 (comprising ppt-cts) and FIG. 3 (comprising ppt-cts and WPRE), except that the luciferase reporter was substituted for eGFP.

Addition of WPRE to the Gene Transfer Vector Further Enhances Infectivity and/or Gene Expression Infectivity of the trans-lentiviral vector of the present invention was further enhanced through the use of a gene transfer vector containing the posttranscriptional regulatory element of woodchuck hepatitis virus (WPRE). Zufferey et al. (1999) *J. Virol.* 73:2886-2892. While the inclusion of a WPRE sequence increased trans-lentiviral titer independent of the inclusion of PPT-CTS sequences, a cumulative enhancement in trans-lentiviral infectivity resulted using a gene transfer vector including PPT, CTS and WPRE, as shown in FIG. 3. Substitution of the gene transfer vector pCMV-PPT-CTS-eGFP-WPRE for the gene transfer vector shown in FIG. 1 enhanced trans-lentiviral vector titer by more than a factor of 2 over that of the vector depicted in FIG. 1 (data not shown). It was also noteable that the level of gene expression in primary cultures of terminally differentiated macrophages was markedly increased with the inclusion of WPRE (FIG. 4). Without WPRE the level of trans-gene expression (GFP) was barley detectable (data not shown). This affect of WPRE on transduction and gene expression is further illustrated in FIG. 7, which shows transduction of cells in the airway of mice using a gene transfer vector as depicted in FIG. 1 (with cts-ppt) and FIG. 3 (with cts-ppt, without WPRE), except that the luciferase reporter was substituted for eGFP.

It is appreciated that while the present invention is detailed in regard to HIV based trans-lentiviral vectors, other lentiviral configurations are anticipated to be equally operative herein, nonexhaustively illustrated by, e.g., SIV, FIV, EIAV and BIV.

Example 4

Transduction of Non-dividing Cells

The trans-lentiviral and lentiviral vectors of the invention readily infect both dividing and non-dividing cells, as gauged by success using and CD34+ bone marrow cells.

Macrophages. Terminally differentiated macrophages were infected with trans-lentiviral vector particles at an MOI of 5. Approximately 20% of the macrophages were positive for GFP expression five days after infection (FIG. 4A). After 14 days, greater than 60% of the macrophages were GFP positive. The transduction efficiency of the trans-lentiviral vector is similar to that of the lentiviral vector (FIG. 4B). Only an occasional weak GFP positive cell is observed in macrophages infected with VSV-G pseudotyped MLV vector particles (data not shown). These results indicate that the requirements for transducing nondividing cells are preserved in the trans-lentiviral vector. The results also demonstrate that the WPRE sequence significantly improves trans-gene expression in primary non-dividing cells.

Figure 5:
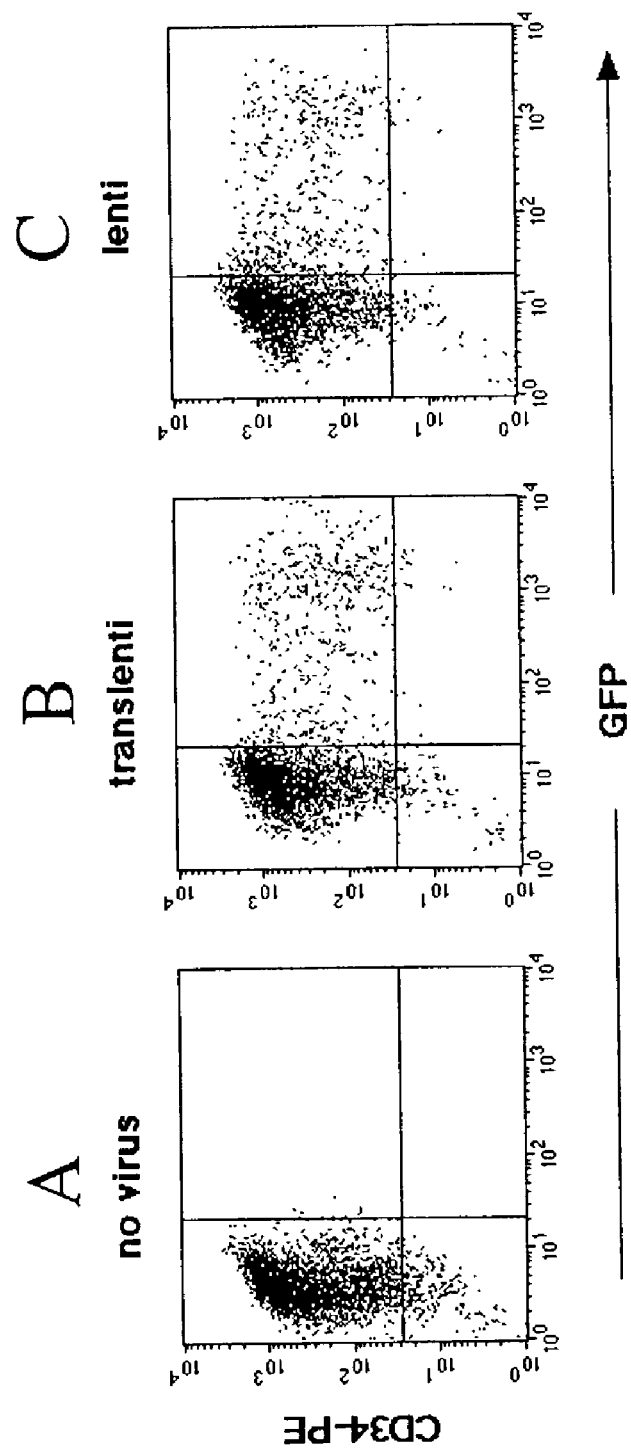
FIG. 5 illustrates trans-gene (eGFP) expression in CD34+ bone marrow cells after transduction with no vector (control, A), trans-lentiviral vector (B) and lentiviral vector (C) as derived in FIG. 4.

CD34+ cells. Recently, an HIV based lentiviral vector system was shown to transduce human CD34+ cells. Akkina et al. (1996) *J. Virology* 70(4):2581-2585. Subsequently, Myoshi et al. demonstrated that transduced cells of this type were capable of stable engraftment in NOD/SCID mice. Miyoshi et al. (1999) *Science* 283:682-686. To analyze whether a trans-lentiviral vector could transduce nonstimulated (without prior treatment with cytokines and/or growth factors) stem cells, CD34+cells were isolated from human bone marrow aspirates using magnetic cell sorting (Luhovy, et al. (1996) *Biology of Blood and Marrow Transplantation* 2:24-30) and immediately transduced with the trans-lentiviral vector similar to that of FIG. 1. To minimize cycling and maintain the pluripotent nature, the cells were kept in media free of serum and exogenous cytokines until after transduction. The CD34+ cells ($2.5 \times 10^5$) were infected for 4 hours using an MOI of 5. For comparison, CD34+ cells were infected with a lentiviral vector similar to that of FIG. 2 in a parallel experiment. Both the lenti- and trans-lentiviral vectors were derived using the gene transfer vector containing WPRE, as shown in FIG. 3. The cells were then cultured for three days in serum-free media containing 20 ng/ml of interleukin-3 (IL-3), stem cell factor (SCF) and GM-CSF. 21.5% of the cells infected with the trans-lentiviral and 22.4% of the lentiviral vector infected cells vector were determined to be GFP positive. See FIG. 5. Control cells not exposed to a viral vector showed no GFP production. FACS analysis indicated that 94% of the transduced cells retained the CD34+ phenotype. This result indicates that the trans-lentiviral vector can efficiently transduce unstimulated CD34+cells.

Figure 6:
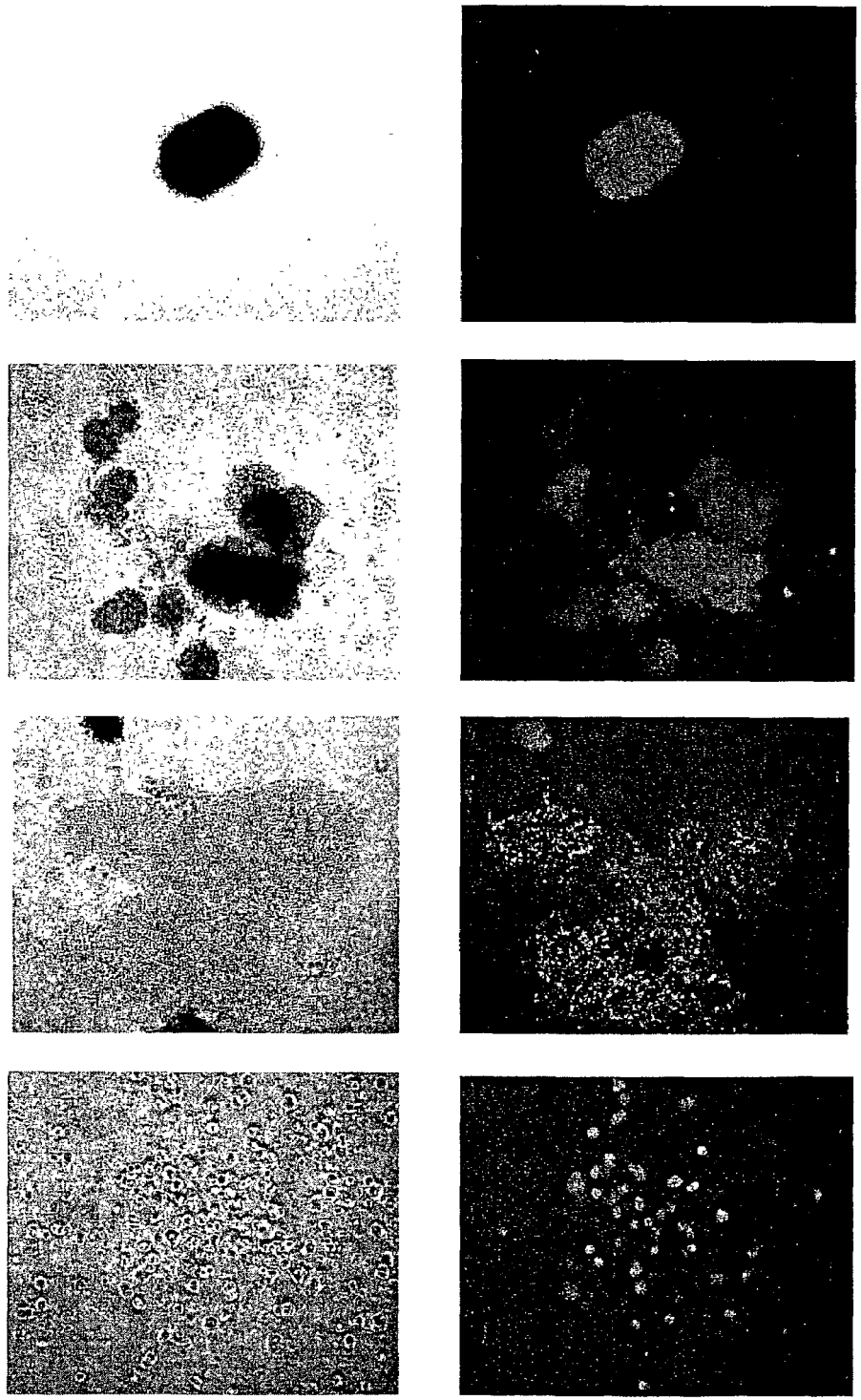
FIG. 6 differentiating cells originating from progenitor CD34+ bone marrow cells transduced with eGFP containing vector (from FIG. 5). Row A depicts bright field micrographs and row B depicts fluorescence micrographs.

As shown in FIG. 6, the transduced CD34+ cells were analyzed in a clonogenic assay by culture in semi-solid medium. As shown, marker gene expression is maintained after cell differentiation. Specifically, FIG. 6 shows stem cell progeny expressing GFP in differentiated forms under bright field (FIG. 6A) and dark field fluorescence (FIG. 6B) microscopy. Cell colonies representing different cell lineages were detected and were GFP+, including CFU-M, BFU-E, CFU-GEMM. Similar results were obtained for the lentiviral and trans-lentiviral vectors of the present invention including those of FIGS. 1 and 3.

Hematopoietic stem cells. Hematopoietic stem cells are CD34+ and have the capacity for self renewal and differentiation into any of the mature cells of the blood, and even other tissue types. Therefore, many diseases can potentially be treated using stable introduction of therapeutic genes into stem cells according to the invention. Subsequent to the filing of the priority application, we, in collaboration with others, validated the feasibility of such an approach using human stem cells transduced with a lentiviral vector containing a GFP reporter gene. Chen et al. (2000) *Stem Cells* 18:352-359. The transduced cells were successfully transplanted into lethally irradiated C57B1/6 mice, where differentiation was determined by GFP expression detected in peripheral mononuclear cells, peripheral blood B cells, T cells, granulocytes and monocytes, bone marrow erythroid precursor cells, splenic B cells, and thymic T cells. Although that data was generated using a lentiviral vector system, and not a trans-lentiviral system, we have since obtained similar results using such a system (data not shown). The feasibility of our approach is further supported by recent data obtained in an HIV-1 SIN vector lentiviral system. Guenechea et al. (2000) *Molecular Therapy* 1(6):566573.

Example 5

Cells, HIV-1 Clones and Expression Plasmids

The pHR-CMV-eGFP plasmid was constructed by ligating a PCR amplified DNA fragment containing the eGFP gene (derived from pEGFP-C1; Clontech Laboratories) into the BamHI/XhoI sites of the pHR-CMV-LacZ plasmid. To construct the pCMV-PPT-CTS-eGFP plasmid, a 150 bp sequence of DNA (coordinates 4327 to 4483) containing the central polypurine tract (PPT) and central terminal site (CTS) was PCR amplified from the HIV-1 pSG3 molecular clone (Ghosh et al. (1993) *Virology* 194:858-864) and ligated into the unique ClaI site of pHR-CMV-eGFP. In a vector comprising WPRE, the WPRE sequence was inserted 3' of eGFP. Post-transcriptional regulatory elements, such as WPRE, can be positioned either 3' or 5' to the gene of interest, but it is preferred that they are positioned 3'. The pCMV-gag-pol packaging plasmid was constructed by inserting a EcoRI/BamHI DNA fragment of pSG3 (coordinates 258 to 8384) into the pcDNA3.1 (+) plasmid (InVitrogen) under control of the CMV promoter. The recombinant plasmid was then modified by introducing a 39-base pair deletion in the packaging sequence (ψ), and a 1357-base pair deletion in the envelope gene (coordinates 5827 to 7184). To construct the RT-IN minus pCMV-gag-pro packaging plasmid, an RT-IN-containing DNA fragment (coordinates 1975 to 5337) of pCMVgag-pol was excised using BclI and SalI and substituted with an RT-IN containing DNA fragment of pSG3S-RT, which contained translational stop codons (TAA) at the first amino acid positions of the RT and IN coding regions (Wu et al. (1997) *EMBO* 16:5113-5122). A frame shift mutation was introduced in the Vpr coding sequence of the pCNW-gag-pol and pCMVgag-pro packaging plasmids by blunt-end ligation at the SalI site, generating pCMV-gag-pol Δvpr and pCMVgag-pro Δvpr, respectively. The packaging plasmids contained functional vif, tat, and rev genes. The pMD-G, pLR2P-vprR-TIN, and pCMV-tat expression plasmids have been described earlier. Wu et al. (1997) *EMBO* 16:5113-5122; Bums et al. (1993) *Proc. Natl. Acad. Sci. USA* 90: 8033-8037; Ory et al. (1996) *PNAS* 93:11400.

One of skill in the art can readily construct equivalent vectors using the genetic element delineations for the HIV-1 genome as reflected in FIG. 1 and Table II (based on NCBI Genbank Genome Accession Number AF033819; SEQ ID No: 1) and that sequences for other lentiviruses are also available and can be used to construct vectors and vector systems directed to a given host species of animal. A more detailed explanation of these components and their function may be found in Coffin et al. (1997) *Retroviruses*, Cold Spring Harbor Laboratory Press, New York, of which the skilled artisan is aware. Those of skill will appreciate that allelic variations can exist between different isolates. In construction of the actual vectors described herein, isolates as described in Li et al. (1992) *J. Virol.* 66:6587 and Ghosh et al. (1993) *Virology* 194:858 were used.

TABLE 11

Genetic Elements and Coordinates of a Human HIV-1 Isolate

| Genetic Element | Coordinates |
|---|---|
| R: | (1-96) |
| U5: | (97-181) |
| PBS: | (182-199) |
| gag: | (336-1836) |
| pro: | (1637-2099) |
| pol: | (2102-4640) |
| vif: | (4587-5163) |
| vpr: | 5105-5339) |
| tat: | (5377-5591, 7925-7968) |
| rev: | (5516-5591, 7925-8197) |
| vpu: | (5608-5854) |
| env: | (5771-8339) |
| nef. | (8343-8710) |
| PPT: | (8615-8630) |
| U3: | (8631-9085) |
| R: | (9086-9181) |

Other components of the various vectors are readily available commercially, or else reproducible without undue experimentation by one of ordinary skill in the art using well-known principles and knowledge within the art.

Example 6

Preparation of Vector Stocks

Preparation of Vector Stocks. Lentiviral vector stocks were produced by transfecting 5 µg of the pCMV-gag-pol packaging plasmid, 2 µg of the pMD-G (VSV-G) expression plasmid, and 5 µg of the gene transfer (vector) plasmid into subconfluent monolayer cultures of 293T cells by the calcium phosphate precipitation method. "Trans-lentiviral" vector stocks were produced by transfecting 5 µg of the pCMV-gag-pro packaging plasmid, 1.5 µg of the pLR2P-vpr-RTIN plasmid, 2 µg of the pMD-G expression plasmid, and 5 µg of the gene transfer (vector) plasmid into subconfluent monolayer cultures of 293T cells. Supernatants were harvested after 60 hrs, clarified by low speed centrifugation (1000 g, 10 min), filtered through 0.45-µm pore-size filters, aliquoted and frozen at −80° C.

Example 7

Infection Target cells were infected with the vector stocks in DMEM containing 1% FBS for 4 hrs at 37° C. The medium was then replaced with fresh DMEM containing 10% FBS.

Example 8

Titering the Vector Stocks

To determine vector titers, supernatant stocks of 1.0, 0.2, 0.04, and 0.008 µl are used to infect cultures of HeLa cell, and GFP positive (green) cell colonies are counted using a fluorescence microscope two days later.

Example 9

Assays To Monitor Gene Delivery

If the heterologous nucleic acid sequence of interest consists of a reporter gene or antibiotic resistance gene, one may merely monitor that effect, e.g., by supplying an appropriate amount of antibiotic sufficient to kill non transduced cells. If the reporter gene is GFP, Bgal, or luciferase, one may use standard methodologies to detect expression of the reporter, e.g., using a luminometer in the case of luciferase, adding a chromogenic substrate such as Xgal in the case of Bgal, or simply monitoring for green fluorescence with an appropriate filtered camera or microscopy device.

If the heterologous nucleic acid sequence consists of a gene for use in gene therapy and one knows of a phenotype differential in transduced versus nontransduced cells, one simply monitors for this. In yet other systems, this can be determined inferentially by supplying a reporter or marker gene on the same construct as the therapeutic gene such that the marker or reporter's activity similarly suggests the activity of the therapeutic gene. Those of skill in the art will appreciate the wide latitude of potential applications.

PCR analyses may also be performed to determined whether a given provirus and its corresponding heterologous nucleic acid sequence of interest has been integrated into a host cell's genome.

This particular application claims priority to several related applications. The claim element terms herein should be construed consistently between the applications to the extent possible, and where not possible, to preserve the broadest reasonable claim scope that is free of the prior art.

All patents and publications mentioned in the specification are indicative of the levels of skill of those skilled in the art to which the invention pertains. All references cited in this disclosure are incorporated by reference to the same extent as if each reference had been incorporated by reference in its entirety individually. One skilled in the art would readily appreciate that the present invention is well adapted to carry out the objects and obtain the ends and advantages mentioned, as well as those inherent. The methods and systems described herein are exemplary and not intended as limitations on the scope of the invention. It will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

That which is claimed:

1. A transretroviral vector system comprising:
   a) at least a first polynucleotide sequence comprising at least one nucleotide sequence encoding a polypeptide selected from the group consisting of:
      i) a functional portion of a Reverse Transcriptase polypeptide; and,
      ii) a functional portion of an Integrase polypeptide;
   wherein said first polynucleotide sequence does not encode a functional Gag polypeptide; and,
   b) a second polynucleotide sequence comprising a nucleotide sequence encoding at least a functional portion of a Gag polypeptide and a functional portion of a protease polypeptide, and said second polynucleotide sequence does not encode at least one of a functional Reverse Transcriptase polypeptide and a functional Integrase polypeptide and said second polypeptide is capable of expression in a mammalian cell; and,
   c) a third polynucleotide sequence comprising a nucleic acid sequence encoding a functional portion of an envelope polypeptide capable of mediating recognition and entry of the viral particle into a target cell, wherein said third polynucleotide sequence does not encode a functional Gag-Pol precursor polypeptide;
   d) a fourth polynucleotide sequence comprising a heterologous nucleic acid sequence of interest and at least one nucleotide sequence is selected from the group consisting of a functional equivalent of a polypurine tract-central terminator sequence (PPT-CTS), a functional equivalent of Woodchuck Hepatitis Virus Post transcriptional Regulatory Element (WPRE), a PPT-CTS, and a WPRE;

wherein the functional portions of the Reverse Transcriptase, Integrase, Gag and protease polypeptides are from a retrovirus and said transretroviral vector system produces a viral particle capable of introducing said heterologous nucleotide sequence of interest into the genome of the target cell.

2. The transretroviral vector system of claim 1 wherein said first polynucleotide sequence encodes at least one fusion protein comprising a functional portion of a Vpr or a Vpx polypeptide fused in frame to the functional portion of a Reverse Transcriptase polypeptide fused in frame to the functional portion of an Integrase polypeptide, said first polynucleotide sequence capable of expression in the mammalian cell, said functional portion of said Vpr or said Vpx polypeptide is capable of providing for the incorporation of said fusion protein into a viral particle.

3. The transretroviral vector system of claim 2, wherein said nucleotide sequence is selected from the group consisting of the PPT-CTS and the WPRE.

4. The transretroviral vector system of claim 2, wherein said heterologous nucleic acid sequence of interest encodes a polypeptide.

5. The transretroviral vector system of claim 4, wherein said polypeptide is selected from the group consisting of a viral inhibitory polypeptide and a therapeutic polypeptide.

6. The transretroviral vector system of claim 2, wherein said first polynucleotide sequence further comprises a Rev Responsive Element (RRE).

7. The transretroviral vector system according to claim 2, further comprises promoters operatively linked to at least one of said first, said second, said third, or said fourth polynucleotide sequences.

8. The transretroviral vector system of claim 2, wherein said heterologous nucleic acid sequence of interest is operably linked to a promoter active in said target cell.

9. The transretroviral vector system of claim 1, wherein the first polynucleotide sequence comprises a nucleotide sequence encoding at least a first fusion protein comprising a functional portion of a first Vpr or a first Vpx polypeptide fused in frame to a functional portion of the Reverse Transcriptase polypeptide, said first polynucleotide sequence capable of expression in the mammalian cell, said functional portion of said first Vpr or said first Vpx polypeptide capable of providing for the incorporation of said fusion protein into a viral particle; and a fifth polynucleotide sequence encoding at least a second fusion protein comprising a functional portion of a second Vpr polypeptide or a second Vpx polypeptide fused in frame to the functional portion of an Integrase polypeptide, said fifth polynucleotide sequence being from a retrovirus and capable of expression in the mammalian cell, said functional portion of the second Vpr or the second Vpx polypeptide capable of providing for the incorporation of said second fusion protein into the viral particle.

10. The transretroviral vector system of claim 9, wherein said nucleotide sequence is selected from the group consisting of the PPT-CTS and the WPRE.

11. The transretroviral vector system of claim 9, wherein said heterologous nucleic acid sequence of interest encodes a polypeptide.

12. The transretroviral vector system of claim 11, wherein said polypeptide is selected from the group consisting of a viral inhibitory polypeptide and a therapeutic polypeptide.

13. The transretroviral vector system of claim 9, wherein said first polynucleotide sequence further comprises an RRE.

14. The transretroviral vector system of claim 9, further comprising promoters operatively linked to at least one of said first, said second, said third, said fourth, or said fifth polynucleotide sequences.

15. The transretroviral vector system according to claim 9, wherein said heterologous nucleic acid sequence of interest is operably linked to a promoter active in said target cell.

16. A method for delivering a heterologous nucleic acid sequence of interest to a target cell comprising
  a) forming a transretroviral particle using a transretroviral vector system comprising a gene transfer vector having the heterologous nucleic acid sequence of interest operably linked to a promoter active in said target cell, said gene transfer vector further comprises at least one nucleotide sequence selected from the group consisting of a WPRE, a PPT-CTS, a functional equivalent of a WPRE or a functional equivalent of a PPT-CTS;
  b) providing the target cell; and,
  c) transducing said target cell with said transretroviral particle,
wherein said heterologous nucleic acid sequence of interest is integrated into the genome of the target cell.

17. The method of claim 16, wherein said nucleotide sequence comprises a WPRE or a PPT-CTS.

18. The method of claim 16, wherein said target cell is a non-dividing cell.

19. The method of claim 16, wherein said target cell is a primary cell.

20. The method of claim 16, wherein said target cell is a macrophage, a CD34$^+$ cell, or a hematopoietic stem cell.

21. The method of claim 16, wherein said nucleic acid sequence of interest encodes a polypeptide.

22. The method of claim 16, wherein said transretroviral vector system further comprises:
  a) a first polynucleotide sequence encoding at least one fusion protein comprising a functional portion of a Vpr or a Vpx polypeptide fused in frame to a functional portion of a Reverse Transcriptase polypeptide fused in frame to a functional portion of an Integrase polypeptide, said first polynucleotide sequence capable of expression in a packaging cell, said Reverse Transcriptase polypeptide and said Integrase polypeptide being encoded by a portion of said first polynucleotide sequence being from a retrovirus, and said functional portion of said Vpr or said Vpx polypeptide capable of providing for the incorporation of said fusion protein into the transretroviral particle;
  b) a second polynucleotide sequence comprising a nucleotide sequence encoding a functional portion of a Gag polypeptide and a functional portion of a Protease polypeptide, said second polynucleotide sequence capable of expression in the packaging cell, said Gag polypeptide and said Protease polypeptide being encoded by a portion of said second polynucleotide sequence being from a retrovirus, and wherein said second polynucleotide sequence does not encode a functional Reverse Transcriptase polypeptide or a functional Integrase polypeptide; and,
  c) a third polynucleotide sequence comprising a nucleic acid sequence encoding an envelope polypeptide capable of mediating recognition and entry of the transretroviral particle into the target cell, wherein said third polynucleotide sequence does not encode a functional Gag-Pol precursor polypeptide.

23. The method of claim 22, wherein said target cell is a non-dividing cell.

24. The method of claim 22, wherein said target cell is a primary cell.

25. The method of claim 22, wherein said target cell is a macrophage, a CD34$^+$ cell, or a hematopoietic stem cell.

26. The method of claim 22, wherein said heterologous nucleic acid sequence of interest encodes a polypeptide.

27. The method of claim 16, wherein said transretroviral vector system further comprises:
   a) a first polynucleotide sequence encoding at least a first fusion protein comprising a functional portion of a Vpr or a Vpx polypeptide fused in frame to a functional portion of a Reverse Transcriptase polypeptide, said first polynucleotide sequence capable of expression in a packaging cell, said Reverse Transcriptase polypeptide being encoded by a portion of said first polynucleotide sequence being from a retrovirus, said functional portion of said Vpr or said Vpx polypeptide is capable of providing for the incorporation of said fusion protein into the transretroviral particle;
   b) a second polynucleotide sequence encoding at least a second fusion protein comprising a functional portion of a second Vpr polypeptide or a second Vpx polypeptide fused in frame to a functional portion of an Integrase polypeptide having integrase activity, said second polynucleotide sequence capable of expression in the packaging cell, said Integrase polypeptide being encoded by a portion of said second polynucleotide sequence being from a retrovirus, said functional portion of the second Vpr or the second Vpx polypeptide capable of providing for the incorporation of said second fusion protein into the transretroviral particle;
   c) a third polynucleotide sequence comprising a nucleotide sequence encoding at least a functional portion of a Gag polypeptide and a functional portion of a Protease polypeptide, said third polynucleotide sequence capable of expression in the packaging cell, said Gag polypeptide and said Protease polypeptide being encoded by a portion of said third polynucleotide sequence being from a retrovirus, and wherein said third polynucleotide sequence does not encode a functional Reverse Transcriptase polypeptide or a functional Integrase polypeptide; and,
   d) a fourth polynucleotide sequence comprising a nucleic acid sequence encoding an envelope polypeptide capable of mediating recognition and entry of the transretroviral particle into the target cell wherein said fourth nucleotide acid segment does not encode a functional Gag-Pol precursor polypeptide.

28. The method of claim 27, wherein said target cell is a non-dividing cell.

29. The method of claim 27, wherein said target cell is a primary cell.

30. The method of claim 27, wherein said target cell is a macrophage, a CD34$^+$ cell, or a hematopoietic stem cell.

31. The method of claim 27, wherein said heterologous nucleic acid sequence of interest encodes a polypeptide.

32. A method for delivering a heterologous nucleic acid sequence of interest to a non-dividing target cell comprising:
   a) forming a transretroviral particle using a transretroviral vector system comprising a gene transfer vector having the heterologous nucleic acid sequence of interest operably linked to a promoter active in said non-dividing target cell;
   b) providing the non-dividing target cell; and,
   c) transducing said non-dividing target cell with the transretroviral particle;

wherein said heterologous nucleic acid sequence of interest is integrated into the genome of the target cell and said gene transfer vector further comprises at least one nucleotide sequence selected from the group consisting of a WPRE, a PPT-CTS, a functional equivalent of WPRE and a functional equivalent of PPT-CTS.

33. The method of claim 32, wherein said nucleotide sequence is selected from the group consisting of the WPRE and the PPT-CTS.

34. The method of claim 32, wherein said non-dividing cell is a primary cell.

35. The method of claim 32, wherein said non-dividing cell is a macrophage, a CD34$^+$ cell, or a hematopoietic stem cell.

36. The method of claim 32, wherein said transretroviral vector system further *comprises*:
   a) a first polynucleotide sequence encoding at least one fusion protein comprising a functional portion of a Vpr or a Vpx polypeptide fused in frame to a functional portion of a Reverse Transcriptase polypeptide fused in frame to a functional portion of an Integrase polypeptide, said first polynucleotide sequence capable of expression in a packaging cell, said Reverse Transcriptase polypeptide and said Integrase polypeptide being encoded by a portion of said first polynucleotide sequence being from a retrovirus, and said functional portion of said Vpr or said Vpx polypeptide capable of providing for the incorporation of said fusion protein into the transretroviral particle;
   b) a second polynucleotide sequence comprising a nucleotide sequence encoding a functional portion of a Gag polypeptide and a functional portion of a Protease polypeptide, said second polynucleotide sequence capable of expression in the packaging cell, said Gag polypeptide and said Protease polypeptide being encoded by a portion of said second polynucleotide sequence being from a retrovirus, and wherein said second polynucleotide sequence does not encode a functional Reverse Transcriptase polypeptide or a functional Integrase polypeptide; and,
   c) a third polynucleotide sequence comprising a nucleic acid sequence encoding an envelope polypeptide capable of mediating recognition and entry of the transretroviral particle into the non-dividing target cell, wherein said third polynucleotide sequence does not encode a functional Gag-Pol precursor polypeptide.

37. The method of claim 36, wherein said nucleic acid sequence comprises the WPRE or the PPT-CTS.

38. The method of claim 36, wherein said non-dividing target cell is a macrophage, a CD34$^+$ cell, or a hematopoietic stem cell.

39. The method of claim 36, wherein said non-dividing target cell is a primary cell.

40. The method of claim 32, wherein said transretroviral vector system further comprises:
   a) a first polynucleotide sequence encoding at least a first fusion protein comprising a functional portion of a Vpr or a Vpx polypeptide fused in frame to a functional portion of a Reverse Transcriptase polypeptide, said first polynucleotide sequence capable of expression in a packaging cell, said Reverse Transcriptase polypeptide being encoded by a portion of said first polynucleotide sequence being from a retrovirus, said functional portion of said Vpr or said Vpx polypeptide capable of providing for the incorporation of said fusion protein into the transretroviral particle;
   b) a second polynucleotide sequence encoding at least a second fusion protein comprising a functional portion of a second Vpr polypeptide or a second Vpx polypeptide fused in frame to a functional portion of an Integrase polypeptide, said second polynucleotide sequence capable of expression in the packaging cell, said Integrase polypeptide being encoded by a portion of said second polynucleotide sequence being from a retrovirus, said functional portion of the second Vpr or the second Vpx polypeptide capable of providing for the incorporation of said second fusion protein into the transretroviral particle;

c) a third polynucleotide sequence comprising a nucleotide sequence encoding at least a functional portion of a Gag polypeptide and a functional portion of a Protease polypeptide, said third polynucleotide sequence capable of expression in the packaging cell, said Gag polypeptide and said Protease polypeptide being encoded by a portion of said third polynucleotide sequence being from a retrovirus, and wherein said third polynucleotide sequence does not encode a functional Reverse Transcriptase polypeptide or a functional Integrase polypeptide; and, d) at least a fourth polynucleotide sequence comprising a nucleic acid sequence encoding an envelope polypeptide capable of mediating recognition and entry of the transretroviral particle into the target cell wherein said third polynucleotide sequence does not encode a functional Gag-Pol precursor polypeptide.

41. The method of claim 40, wherein said nucleotide sequence comprises the WPRE or the PPT-CTS.

42. The method of claim 40, wherein said non-dividing cell is a macrophage, a $CD34^+$ cell, or a hematopoietic stem cell.

43. The method of claim 40, wherein said non-dividing cell is a primary cell.

* * * * *

SEQUENCE LISTING

<160> NUMBER OF SEQ ID NOS: 3

<210> SEQ ID NO 1
<211> LENGTH: 592
<212> TYPE: DNA

-continued

```
<213> ORGANISM: Woodchuck hepatitis virus
<220> FEATURE:
<221> NAME/KEY: misc_feature
<222> LOCATION: (0)...(0)
<223> OTHER INFORMATION: WPRE element

<400> SEQUENCE: 1
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aacccccact     240
ggttggggca ttgccaccac ctgtcagctc ctttccggga cttttcgcttt cccctccct    300 attgccacgg cggaactcat cgccgcctgc cttgcccgct gctggacagg ggctcggctg     360
ttgggcactg acaattccgt ggtgttgtcg gggaagctga cgtcctttcc atggctgctc     420
gcctgtgttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgcc tg             592

<210> SEQ ID NO 2
<211> LENGTH: 114
<212> TYPE: DNA
<213> ORGANISM: Human Immunodeficiency Virus
<220> FEATURE:
<221> NAME/KEY: misc_feature
<222> LOCATION: (0)...(0)
<223> OTHER INFORMATION: PPT-CTS

<400> SEQUENCE: 2
aaaagaaaag gggggattgg ggggtacagt gcagggggaaa gaatagtaga cataatagca     60
acagacatac aaactaaaga actacaaaaa caaattacaa aaattcaaaa tttt           114

<210> SEQ ID NO 3
<211> LENGTH: 15
<212> TYPE: DNA
<213> ORGANISM: Human Immunodeficiency Virus
<220> FEATURE:
<221> NAME/KEY: misc_feature
<222> LOCATION: (0)...(0)
<223> OTHER INFORMATION: Fragment of PPT sequence

<400> SEQUENCE: 3
aaaagaaaag ggggg                                                       15
```